(12) United States Patent
Akimoto et al.

(10) Patent No.: US 8,546,582 B2
(45) Date of Patent: Oct. 1, 2013

(54) SULFENAMIDE, VULCANIZATION ACCELERATOR CONTAINING THE SULFENAMIDE FOR RUBBER, AND PROCESS FOR PRODUCING THE VULCANIZATION ACCELERATOR

(75) Inventors: Keiichi Akimoto, Sukagawa (JP); Nozomi Ariga, Sukagawa (JP); Kyouji Okawa, Sukagawa (JP); Tomoyuki Komatsu, Sukagawa (JP); Hiroshi Shibuya, Sukagawa (JP)

(73) Assignee: Ouchi Shinko Chemical Industrial Co., Ltd., Chuo-Ku (JP)

( * ) Notice: Subject to any disclaimer, the term of this patent is extended or adjusted under 35 U.S.C. 154(b) by 545 days.

(21) Appl. No.: 12/810,071

(22) PCT Filed: Dec. 24, 2008

(86) PCT No.: PCT/JP2008/073440
§ 371 (c)(1),
(2), (4) Date: Sep. 13, 2010

(87) PCT Pub. No.: WO2009/084538
PCT Pub. Date: Jul. 9, 2009

(65) Prior Publication Data
US 2010/0324301 A1 Dec. 23, 2010

(30) Foreign Application Priority Data
Dec. 27, 2007 (JP) .................. 2007-337035

(51) Int. Cl.
*C07D 277/80* (2006.01)

(52) U.S. Cl.
USPC ....................................... 548/168

(58) Field of Classification Search
USPC ....................................... 548/168
See application file for complete search history.

(56) References Cited

U.S. PATENT DOCUMENTS 2,782,202 A * 2/1957 Henderson .................. 548/168
3,658,808 A * 4/1972 Kinstler ...................... 544/135
3,658,828 A 4/1972 D'Amico

FOREIGN PATENT DOCUMENTS

| JP | 48-011214 B | 4/1973 |
| JP | 59-172483 A1 | 9/1984 |
| JP | 2005-139082 A1 | 6/2005 |

OTHER PUBLICATIONS

Extended European Search Report dated Feb. 22, 2011.
C.D. Wacker, et al., "New Sulfenamide Accelerators Derived from 'Safe' Amines for the Rubber and Tire Industry," IARC Scientific Publications, 1991, 105, p. 592-594.
Frederick Ignatz-Hoover, et al., "Delayed Action Accelerated Sulfur Vulcanization of High Diene Elastomers; the Effects of the Amine on Vulcanization Characteristics of Sulfenamide Accelerated Cure Systems," Meeting of the Rubber Division, American Chemical Society, 1994, 145 (Paper No. 3), p. 1-13.

* cited by examiner

*Primary Examiner* — Jason M Nolan
(74) *Attorney, Agent, or Firm* — Burr & Brown

(57) ABSTRACT

A sulfenamide vulcanization accelerator is provided that acts satisfactorily slowly on a vulcanization reaction, produces no carcinogenic nitrosamine, and is free from environmental hygiene problems such as bioaccumulation. Also provided is an N-alkyl-N-t-butylbenzothiazole-2-sulfenamide represented by formula [I]. The vulcanization accelerator is a vulcanization accelerator for rubber, containing this compound. Furthermore provided is a process for producing the vulcanization accelerator.

[Chemical formula 1]

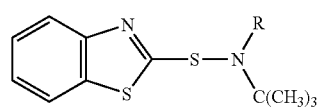

[I]

wherein R represents methyl, ethyl, n-propyl, or n-butyl.

2 Claims, No Drawings

SULFENAMIDE, VULCANIZATION ACCELERATOR CONTAINING THE SULFENAMIDE FOR RUBBER, AND PROCESS FOR PRODUCING THE VULCANIZATION ACCELERATOR

FIELD OF INVENTION

The present invention relates to a novel sulfenamide, a vulcanization accelerator for rubber, comprising the sulfenamide, and a process for producing the vulcanization accelerator.

BACKGROUND ART

In general, N-alkyl- and N,N-dialkylbenzothiazole-2-sulfenamides are used as vulcanization accelerators for rubber and are known generally as sulfenamide vulcanization accelerators. These sulfenamide vulcanization accelerators are characterized in that they act slowly on a vulcanization reaction. Therefore, they are less likely to cause scorching in the heat history of a rubber processing process and thus are used in many rubber products such as tires and rubber vibration isolators. N-Monoalkyl compounds such as N-cyclohexylbenzothiazole-2-sulfenamide (CBS) and N-t-butylbenzothiazole-2-sulfenamide (BBS) and N,N-dialkyl compounds such as N,N-dicyclohexylbenzothiazole-2-sulfenamide (DCBS) are used as sulfenamide vulcanization accelerators, and the N,N-dialkyl compounds are reported to have a larger slow acting effect on the vulcanization reaction than the N-monoalkyl compounds.

In a rubber product production process, N-nitrosamine produced during the rubber processing process or storage of rubber products is pointed out to be carcinogenic, and, for example, the concentration of carcinogenic N-nitrosamine in environments (such as in rubber processing process or warehouses) is regulated by German Technical Regulation on dangerous Substances TRGS552.

N-Nitrosamines produced from primary amines are easily decomposed due to their instability and thus are not acknowledged as a problem, whereas many of N-nitrosamines derived from secondary amines are pointed out to be carcinogenic. On the other hand, the above-described German Technical Regulation on dangerous Substances TRGS552 explicitly states that ten N-nitrosamines including N-nitrosodicyclohexylamine, N-nitrosodibenzylamine, N-nitroso-N-methyl-t-butylamine, N-nitroso-N-ethyl-t-butylamine, and N-nitroso-N-n-butyl-t-butylamine are not carcinogenic (non-patent document 3).

At the present time, in the Ministry of Economy, Trade and Industry, safety checks of existing chemical substances are successively carried out. Tests on the degree of degradation of chemical substances by microorganisms and the like and tests on the level of bioaccumulation or bioconcentration of chemical substances in the body of fish and shellfish are also carried out as part of the safety checks.

In recent years, as a result of safety checks of existing chemical substances for DCBS which is one of sulfenamide vulcanization accelerators widely used in the production of tires and the like, it was confirmed that DCBS is a hardly degradable substance and is highly bioconcentrative (concentration ratio ($BCF_{SS}$)=6000 times: Official Bulletin of Economy, Trade and Industry, Dec. 22, 2005). As a result, DCBS was designated as a Type I Monitored Chemical Substance.

Accordingly, the development of sulfenamide vulcanization accelerators that are safe and can act effectively and slowly on vulcanization has been strongly desired. Accordingly, in designing sulfenamide vulcanization accelerators, it is important that an alkyl group be selected while taking into consideration the fact that the slow acting properties for vulcanization are greatly different depending upon the type of the alkyl chain even when secondary amines are used, as well as measures for solving the problem of N-nitrosamine and bioconcentration of sulfenamides.

In view of the above matters, the present inventors have made extensive and intensive studies and, as a result, have found that N-alkyl-N-t-butylbenzothiazole-2-sulfenamides represented by formula [1]:

[Chemical formula 1]

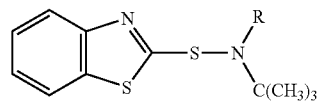

wherein R represents methyl, ethyl, n-propyl, or n-butyl, can be used as vulcanization accelerators that have slow acting properties for a vulcanization reaction equal or superior to DCBS, do not produce carcinogenic N-nitrosamine, and do not cause environmental problems such as bioconcentration. This has led to the completion of the present invention.

Among these compounds, only N-methyl-N-t-butylbenzothiazole-2-sulfenamide (BMBS) have a registry number (registry No. 139361-76-5) in Chemical Substance Registration System in Chemical Abstracts Service (CAS Registry Number (139361-76-5)). Non-patent document 4 which is a sole document cited from the Chemical Substance Registration System describes that N-methyl-N-t-butylbenzothiazole-2-sulfenamide (BMBS) has the same vulcanization behavior as CBS. In non-patent document 4, however, there is no description on specific experimental facts, for example, synthetic methods for samples used, chemical and spectroscopic properties of the samples, the type and compounding amount of rubbers used for evaluation, experimental results on vulcanization behavior including scorch time, and dynamic property values of the resultant vulcanized rubbers, and the basis on which the authors of non-patent document 4 conclude that N-methyl-N-t-butylbenzothiazole-2-sulfenamide (BMBS) has the same vulcanization behavior as CBS is unknown at all.

N-Ethyl-N-t-butylbenzothiazole-2-sulfenamide (BEBS), N-n-propyl-N-t-butylbenzothiazole-2-sulfenamide (BPBS), and N-n-butyl-N-t-butylbenzothiazole-2-sulfenamide (BBBS) are not, of course, reported to have been synthesized and do not have a registry number in Chemical Substance Registry System in Chemical Abstracts Service. Further, it is a matter of course that there is no report about the use of these compounds as vulcanization accelerators. Sulfenamides containing a branched alkyl group on nitrogen, for example, N-(2-alkyl)-N-t-butylbenzothiazole-2-sulfenamides, are described in patent document 1. These sulfenamides are characterized in that they per ser are solid at ordinary temperature. Due to this characteristic feature, the alkyl group on located nitrogen is limited to one tertiary alkyl and one secondary alkyl or cycloalkyl, and patent document 1 does not refer to sulfenamides according to the present invention in which the alkyl groups on located nitrogen are one t-butyl group and one primary alkyl group. Further, patent document 1 has no description on safety and hygiene, for example, carcinogenesis of N-nitrosamine produced from the corresponding sulfenamide and the accumulation or concentration of sulfenamide.

Further, regarding synthesis methods for sulfenamides, sulfenamides are generally synthesized by adding chlorine or sodium hypochlorite into a mixture of a salt of 2-mercaptobenzothiazole or bis(benzothiazol-2-yl)disulfide with a corresponding amine. This synthetic method, however, results in the inclusion of many impurities in a product. The present inventor has also made extensive and intensive studies on this matter and, as a result, has found that high-purity sulfenamides can be produced by a production process comprising previously reacting amine with chlorine or sodium hypochloride to give N-chloroamine and then reacting N-chloroamine with bis(benzothiazol-2-yl)disulfide in the presence of a base in an organic solvent.

Non-patent document 1: Chikosei Karyuyo Yakuzai Toshiteno S—N Kagobutsu (S—N compounds as slow acting vulcanization agent) (part 1), NIPPON GOMU KYOKAI-SHI, Vol. 51, No. 11, 1978, p. 842-852

Non-patent document 2: Chikosei Karyuyo Yakuzai Toshiteno S—N Kagobutsu (S—N compounds as slow acting vulcanization agent) (part 3), NIPPON GOMU KYOKAI-SHI, Vol. 52, No. 1, 1979, p. 34-40

Non-patent document 3: Technische Regeln fur Gefahrstoffe TRGS 552 N-Nitrosoamine (2007)

Non-patent document 4: IARC Scientific Publications, 105, 592 (1991)

Patent document 1: Japanese Patent Publication No. 11214/1973

DISCLOSURE OF INVENTION

Problems to be Solved by the Invention

The present invention provides a sulfenamide vulcanization accelerator that does not produce carcinogenic N-nitrosamine in a rubber product production process, is free from an environmental hygiene problem such as bioconcentration, and satisfactorily slowly acts on a vulcanization reaction.

Means for Solving Problems

The present inventors have found that compounding of a specific novel vulcanization accelerator, that is, an N-alkyl-N-t-butylbenzothiazole-2-sulfenamide in which the alkyl group is methyl, ethyl, n-propyl, or n-butyl, into a diene rubber, that is, a rubber ingredient that can be vulcanized using sulfur as a crosslinking agent can impart slow acting properties for vulcanization equal or superior to those of widely used DCBS, in a vulcanization process of a diene rubber.

Thus, according to one aspect of the present invention, there is provided an N-alkyl-N-t-butylbenzothiazole-2-sulfenamide represented by formula [I]:

[Chemical formula 2]

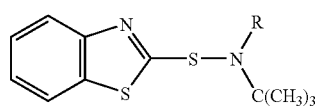

[I]

wherein R represents ethyl, n-propyl, or n-butyl.

According to another aspect of the present invention, there is provided a vulcanization accelerator for rubber characterized by comprising an N-alkyl-N-t-butylbenzothiazole-2-sulfenamide represented by formula [II]:

[Chemical formula 3]

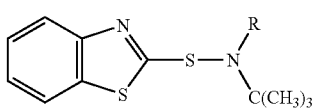

[II]

wherein R represents methyl, ethyl, n-propyl, or n-butyl.

According to a further aspect of the present invention, there is provided a process for producing an N-alkyl-N-t-butylbenzothiazole-2-sulfenamide represented by formula [II], the process being characterized by comprising reacting an N-alkyl-N-t-butylchloroamine represented by formula [III] with bis(benzothiazol-2-yl)disulfide in the presence of a base in a solvent:

[Chemical formula 4]

[III]

wherein R represents methyl, ethyl, n-propyl, or n-butyl.

N-Nitroso-N-methyl-t-butylamine, N-nitroso-N-ethyl-t-butylamine, and N-nitroso-N-n-butyl-t-butylamine that, when the N-alkyl-N-t-butylbenzothiazole-2-sulfenamide according to the present invention is used, are expected to be produced in a rubber product production process are substances which are explicitly stated as a noncarcinogenic N-nitrosamine in German Technical Regulation TRGS552. Further, also in a preliminary test on accumulation or concentration, it is suggested that sulfenamides have low bioconcentration in fish and shellfish.

Effect of the Invention

Compounding of the vulcanization accelerator according to the present invention can realize a satisfactory slow acting effect for a vulcanization reaction of a diene rubber and can reduce the possibility of causing scorch in heat history in a rubber processing process.

The vulcanization accelerator according to the present invention is particularly suitable for the production of tires.

Further, unlike the use of vulcanization accelerators derived from secondary amines which have a possibility of producing carcinogenic N-nitrosamine in the production process, N-nitrosamine derived from the vulcanization accelerator according to the present invention has already been confirmed to be safe and thus does no pose an environmental problem.

Also from the viewpoint of bioconcentration which is acknowledged as a problem in DCBS, the sulfenamide compound according to the present invention can be said to be a safe substance.

BEST MODE FOR CARRYING OUT THE INVENTION

The vulcanization accelerator according to the present invention can be mainly used in the step of vulcanizing a diene rubber with sulfur. Such diene rubbers include natural rubbers, butadiene rubbers, styrene-butadiene rubbers, isoprene rubbers, butyl rubbers, acrylonitrile-butadiene rubbers, chloroprene rubbers, and ethylene-propylene-diene rubbers. These diene rubbers can be used either solely or as a mixture of two or more. The type and concrete contents of diene rubbers, the ratio between a plurality of diene rubbers when the plurality of diene rubbers are used and the like can be properly determined depending, for example, upon concrete applications, purposes and the like.

The content of the N-alkyl-N-t-butylbenzothiazole-2-sulfenamide represented by formula [I] according to the present invention is preferably 0.2 to 10 parts per hundred rubber (by weigh based on 100 parts by weight of the dine rubber; hereinafter the definition is the same). The contemplated effect of the present invention can be attained by compounding N-alkyl-N-t-butylbenzothiazole-2-sulfenamide in the above-defined amount range. When the content of the N-alkyl-N-t-butylbenzothiazole-2-sulfenamide is less than 0.2 part per hundred rubber, the degree of crosslinking is excessively low. On the other hand, when the content of the N-alkyl-N-t-butylbenzothiazole-2-sulfenamide is more than 10 parts per hundred rubber, the degree of vulcanization is so high that the properties of the vulcanized rubber are adversely affected. The content of the N-alkyl-N-t-butylbenzothiazole-2-sulfenamide is particularly preferably 0.3 to 3.0 parts per hundred rubber.

The vulcanization accelerator according to the present invention contains the N-alkyl-N-t-butylbenzothiazole-2-sulfenamide represented by formula [II]. Accordingly, the vulcanization accelerator according to the present invention includes one consisting essentially of the N-alkyl-N-t-butylbenzothiazole-2-sulfenamide represented by formula [II] and one comprising the N-alkyl-N-t-butylbenzothiazole-2-sulfenamide represented by formula [II] as a main ingredient and various accessory ingredients. Examples of such accessory ingredients include small amounts of by-products derived, for example, from the production process and various materials used also in conventional vulcanization accelerators, for example, stabilizers, shape retaining agents, oils, vehicles, tackifier, and powders (for example, preferably silica and alumina).

Preferably, the vulcanization accelerator according to the present invention contains not less than 85% by weight of the N-alkyl-N-t-butylbenzothiazole-2-sulfenamide represented by formula [II]. The content of the N-alkyl-N-t-butylbenzothiazole-2-sulfenamide represented by formula [II] is particularly preferably not less than 90% by weight, especially preferably not less than 95% by weight.

If necessary, the vulcanization accelerator according to the present invention may also be used as a mixture with powders of carbon black, silica, alumina, aluminosilicate (for example, montmorillonite) and the like commonly used in rubbers. The use of the vulcanization accelerator according to the present invention as the mixture can allow the properties or characteristics of the vulcanization accelerator according to the present invention, for example, the shape of particles, particle diameters, stability, reactivity, and melting point (mp), to be easily regulated and thus can contribute to further improved convenience or usability of the vulcanization accelerator in each stage of the production, transport, storage, and use of the vulcanization accelerator. Although the optimal compounding amount range of the powder may vary depending upon the type and purpose of compounding of the powder, the amount of the powder is preferably 1 to 100 parts by weight, particularly preferably 25 to 50 parts by weight, based on 100 parts by weight of the N-alkyl-N-t-butylbenzothiazole-2-sulfenamide represented by formula [II].

In the N-alkyl-N-t-butylbenzothiazole-2-sulfenamide represented by formula [I] or formula [II] according to the present invention, a compound in which R in the formula represents methyl is preferred from the viewpoint of the lowest bioconcentration, and compounds in which R in the formula represents ethyl, n-propyl, and n-butyl are preferred from the viewpoint of a high level of slow acting properties for vulcanization. A compound in which R represents ethyl is particularly preferred, for example, from the viewpoint of a balance between bioconcentration and slow acting properties for vulcanization.

In the present invention, a single compound in which the substituent R represents one of the possible substituents may be used, or alternatively a plurality of compounds different from each other in the substituent R may be used in combination.

N-Alkyl-N-t-butylbenzothiazole-2-sulfenamides represented by formula [I] or formula [II] according to the present invention as such function as a vulcanization accelerator and thus can be used solely, that is, without use thereof in combination with other vulcanization accelerator. Alternatively, the N-alkyl-N-t-butylbenzothiazole-2-sulfenamides represented by formula [I] or formula [II] according to the present invention may be used in combination with other vulcanization accelerators or the like other than those according to the present invention. When the N-alkyl-N-t-butylbenzothiazole-2-sulfenamides represented by formula [I] or formula [II] according to the present invention are used as an alternative to DCBS which is currently regarded as posing a problem of high bioconcentration, preferably, DCBS is replaced with a substantially equimolar amount of the N-alkyl-N-t-butylbenzothiazole-2-sulfenamide, and, particularly preferably, a substantially equimolar amount of BEBS is used instead of DCBS. As is also apparent from the working examples in which the compounding of BEBS in an equimolar amount provides vulcanization behavior and initial properties of the vulcanization product equivalent to those of DCBS, the use of BEBS in a molar amount equal to that of DCBS instead of DCBS is reasonable. Further, also from the viewpoint of hygiene, the bioconcentration of the sulfenamide according to the present invention is much smaller than that of DCBS. The shorter the length of the alkyl group, the lower the bioconcentration. It is a matter of course that, since the vulcanization behavior and the properties of the vulcanization product vary depending upon the type of rubber used and compounding, the amount of the N-alkyl-N-t-butylbenzothiazole-2-sulfenamide according to the present invention compounded may be, if necessary, properly varied in the above-defined content range.

The N-alkyl-N-t-butylbenzothiazole-2-sulfenamide represented by formula [I] or formula [II] according to the present invention can easily be produced using bis(benzothiazol-2-yl)disulfide and N-alkyl-t-butylamine as starting compounds.

Preferably, the compound represented by formula [I] or formula [II] can be produced by the following process.

Specifically, N-chloroamine previously prepared by reacting a corresponding amine with sodium hypochlorite is reacted with bis(benzothiazol-2-yl)disulfide in the presence of an amine or a base in a proper solvent. Proper post treatment such as filtration, washing with water, concentration, and recrystallization according to the properties of the resultant reaction mixture provides the contemplated sulfenamide.

Bases usable in the production process according to the present invention include amines (extra amount of amines used as the starting compound), tertiary amines such as triethylamine, alkali hydroxides, alkali carbonates, alkali bicarbonates, and sodium alkoxides. A particularly preferred method comprises carrying out the reaction using an excessive amount of the amine as a base or using triethylamine which is a tertiary amine, neutralizing the resultant hydrochloride with sodium hydroxide, taking out the contemplated product, and recovering the amine from the filtrate for reutilization.

Alcohols are preferred as the solvent used in the production process according to the present invention, and methanol and ethanol are particularly preferred.

EXAMPLES

The present invention is further illustrated by the following Examples that are not intended as a limitation of the technical scope of the invention.

Example 1

Synthesis of
N-ethyl-N-t-butylbenzothiazole-2-sulfenamide
(BEBS)

A 12% aqueous sodium hypochlorite solution (148 g) was added dropwise to 16.4 g (0.162 mol) of N-t-butylethylamine at 0° C. or below, the mixture was stirred for 2 hr, and N-chloro-N-t-butylethylamine was separated as an oil layer. Bis(benzothiazol-2-yl)disulfide (39.8 g, 0.120 mol), 24.3 g (0.240 mmol) of N-t-butylethylamine, and the separated N-chloro-N-t-butylethylamine were suspended in 120 ml of methanol, and the mixture was stirred under reflux for 2 hr. After cooling, the reaction solution was neutralized with 6.6 g (0.166 mol) of sodium hydroxide, was filtered, was washed with water, and was concentrated under the reduced pressure. The concentrate was recrystallized to obtain 41.9 g (yield: 66%) of contemplated BEBS as a white solid (melting point (mp) 60-61° C.).

Spectrum data of BEBS was shown as follows.

$^1$H-NMR (400 MHz, CDCl$_3$) δ=1.29 (t, 3H, J=7.1 Hz, CH$_3$ (ethyl)), 1.34 (s, 9H, CH$_3$ (t-butyl)), 2.9-3.4 (br-d, CH$_2$), 7.23 (1H, m), 7.37 (1H, m), 7.75 (1H, m), 7.78 (1H, m): $^{13}$C-NMR (100 MHz, CDCl$_3$) δ=15.12, 28.06, 47.08, 60.41, 120.70, 121.26, 123.23, 125.64, 134.75, 154.93, 182.63: mass analysis (EI, 70 eV): m/z; 251 (M$^+$-CH$_4$), 167 (M$^+$-C$_6$H$_{14}$N), 100 (M$^+$-C$_7$H$_5$NS$_2$): IR (KBr, cm$^{-1}$): 3061, 2975, 2932, 2868, 1461, 1429, 1393, 1366, 1352, 1309, 1273, 1238, 1198, 1103, 1022, 1011, 936, 895, 756, 727.

Example 2

Synthesis of N-methyl-N-t-butyl benzothiazole-2-sulfenamide (BMBS)

BMBS was obtained as a white solid (46.8 g (yield: 82%), mp 56-58° C.) in the same manner as in Example 1, except that, instead of N-t-butylethylamine, N-t-butylmethylamine was used in amounts of 14.1 g (0.162 mol) and 20.9 g (0.240 mol).

$^1$H-NMR (CDCl$_3$) δ=1.32 (9H, s, CH$_3$ (t-butyl)), 3.02 (3H, s, CH$_3$ (methyl)), 7.24 (1H, m), 7.38 (1H, m), 7.77 (1H, m), 7.79 (1H, m): $^{13}$C-NMR (CDCl$_3$) δ=27.3, 41.9, 59.2, 120.9, 121.4, 123.3, 125.7, 135.0, 155.5, 180.8: mass analysis (EI, 70 eV) m/z 252 (M$^+$), 237 (M$^+$-CH$_3$), 223 (M$^+$-C$_2$H$_6$), 195 (M$^+$-C$_4$H$_9$), 167 (M$^+$-C$_5$H$_{12}$N), 86 (M$^+$-C$_7$H$_4$NS$_2$).

Example 3

Synthesis of N-n-propyl-N-t-butylbenzothiazole-2-sulfenamide (BPBS)

BPBS was obtained as a white solid (41.9 g (yield: 66%), mp 55-56° C.) in the same manner as in Example 1, except that, instead of N-t-butylethylamine, N-t-butyl-n-propylamine was used in amounts of 20.9 g (0.162 mol) and 31.0 g (0.240 mol).

$^1$H-NMR (400 MHz, CDCl$_3$) δ: 7.8-7.2 (4H), 3.12-2.94 (2H, CH$_2$), 1.74 (2H, br, CH$_2$), 1.33 (9H, s, CH$_3$ (t-butyl)), 0.91 (3H, t, J=7.32 Hz, CH$_3$ (n-Pr)); $^{13}$C-NMR (100 MHz, CDCl$_3$) δ: 181.32, 154.85, 134.71, 125.65, 123.23, 121.26, 120.70, 60.34, 55.25, 28.03, 22.99, 11.66; mass analysis (EI, 70 eV) m/z 266; IR (neat): cm$^{-1}$.

Example 4

Synthesis of N-n-butyl-N-t-butylbenzothiazole-2-sulfenamide (BBBS)

BBBS was obtained as a white solid (42.4 g (yield: 60%), mp 55-56° C.) in the same manner as in Example 1, except that, instead of N-t-butylethylamine, N-t-butyl-n-butylamine was used in amounts of 20.9 g (0.162 mol) and 31.0 g (0.240 mol).

$^1$H-NMR (400 MHz, CDCl$_3$) δ=0.89 (3H, t, J=7.32 Hz, CH$_3$ (n-Bu)), 1.2-1.4 (s+m, 11H, CH$_3$ (t-butyl)+CH$_2$ (n-butyl)), 1.70 (br.s, 2H, CH$_2$), 2.9-3.2 (br.d, 2H, N—CH$_2$), 7.23 (1H, m), 7.37 (1H, m), 7.75 (1H, m), 7.78 (1H, m); $^{13}$C-NMR (100 MHz, CDCl$_3$) δ: 14.0, 20.4, 27.9, 31.8, 53.0, 60.3, 120.6, 121.1, 123.1, 125.5, 134.6, 154.8, 181.2; mass analysis (EI, 70 eV) m/z 294 (M$^+$), 279 (M$^+$-CH$_3$), 237 (M$^+$-C$_4$H$_9$), 167 (M$^+$-C$_8$H$_{18}$N), 128 (M$^+$-C$_7$H$_4$NS$_2$): IR (neat): 1707 cm$^{-1}$, 3302 cm$^{-1}$.

Examples 5 to 8 and Comparative Example 1

For N-methyl-N-t-butylbenzothiazole-2-sulfenamide (BMBS) synthesized in Example 1, N-ethyl-N-t-butylbenzothiazole-2-sulfenamide (BEBS) synthesized in Example 2, N-n-propyl-N-t-butylbenzothiazole-2-sulfenamide (BPBS) synthesized in Example 3, N-n-butyl-N-t-butylbenzothiazole-2-sulfenamide (BBBS) synthesized in Example 4, and N,N-dicyclohexylbenzothiazole-2-sulfenamide (DCBS) which is a conventional compound, the 1-octanol/water distribution coefficient was measured by high-performance liquid chromatography according to JIS Z7260-117. The results are shown in Table 1.

TABLE 1

|  |  | logPow | Remarks |
|---|---|---|---|
| Example 5 | BMBS | 4.5 |  |
| Example 6 | BEBS | 4.9 |  |
| Example 7 | BPBS | 5.3 |  |
| Example 8 | BBBS | 5.8 |  |
| Comparative Example 1 | DCBS | 7.4 | Outside scope of application of invention |

Example 9

For BEBS synthesized in Example 2, a test on the degree of bioconcentration of a chemical substance in the body of fish and shellfish was carried out according to "Shinki Kagaku Busshitsu To Nikakaru Shiken No Hoho Nitsuite (Circular on Test Methods of New Chemical Substances)" (Yakushokuhatsu No. 1121002 dated Nov. 21, 2003, Seikyoku No. 2 dated on Nov. 13, 2003, Kanhokihatsu No. 03121002). The results on the bioconcentration ratio are shown in Table 2.

Testing Conditions

Test fish: carp

Test bioconcentration: First bioconcentration area 1 μg/L

Second bioconcentration area 0.1 μg/L

Exposure duration: 22 days

Exposure method: Continuous flow-through

Analytical method: High-performance liquid chromatography

Test Results

TABLE 2

|  | Concentration ratio (times) | | | |
|---|---|---|---|---|
|  | After 14 days | | After 22 days | |
| First concentration area (average) | 120 | 240 | 180 | 170 |
|  | 180 | | 170 | |
| Second concentration area (average) | 180 | 190 | 180 | 130 |
|  | 180 | | 160 | |

Examples 10 to 13 and Comparative Examples 2 and 3

Ingredients described in Table 3 were kneaded at ratios described in the table (unit: % by weight) with a Banbury mixer by a conventional method to give rubber compositions. For the rubber compositions, unvulcanized rubber properties and vulcanized rubber properties were evaluated by the following evaluation methods.

(1) Properties of Unvulcanized Rubber

The scorch time (t5) was measured using a rectangular groove die (Larg rotor) at 125° C. according to JIS K 6300-1. The rate of cure (tc(90)) and the vulcanization torque (MH) were measured at 145° C. according to a die vulcanization testing method B-2 specified in JIS K 6300-2.

(2) Initial Properties of Vulcanized Rubber

Vulcanized rubber was prepared by press vulcanization at 145° C. for 40 min. The tensile strength, elongation at break and tensile stress at 200% were measured at room temperature according to JIS K 6254. The hardness was measured with a type A durometer according to JIS K 6253.

The results on (1) properties of unvulcanized rubber and (2) initial properties of vulcanized rubber were expressed in terms of an index by presuming the results of Comparative Example 3 to be 100. The results are shown in Table 3.

TABLE 3

| | Comp. Ex. 2 | Comp. Ex. 3 | Comp. Ex. 10 | Comp. Ex. 11 | Comp. Ex. 12 | Comp. Ex. 13 |
|---|---|---|---|---|---|---|
| Natural rubber | 100.0 | 100.0 | 100.0 | 100.0 | 100.0 | 100.0 |
| Zinc oxide | 5.0 | 5.0 | 5.0 | 5.0 | 5.0 | 5.0 |
| Stearic acid | 3.0 | 3.0 | 3.0 | 3.0 | 3.0 | 3.0 |
| Carbon black (HAF) | 50.0 | 50.0 | 50.0 | 50.0 | 50.0 | 50.0 |
| Napthenic oil | 10.0 | 10.0 | 10.0 | 10.0 | 10.0 | 10.0 |
| 6PPD *1 | 2.0 | 2.0 | 2.0 | 2.0 | 2.0 | 2.0 |
| TMDQ *2 | 1.0 | 1.0 | 1.0 | 1.0 | 1.0 | 1.0 |
| Sulfur | 3.0 | 3.0 | 3.0 | 3.0 | 3.0 | 3.0 |
| CBS *3 | 1.0 | — | — | — | — | — |
| DCBS *4 | — | 1.0 | — | — | — | — |
| BMBS | — | — | 1.0 | — | — | — |
| BEBS | — | — | — | 1.0 | — | — |
| BPBS | — | — | — | — | 1.0 | — |
| BBBS | — | — | — | — | — | 1.0 |

*1: N-Phenyl-N-(1,3-dimethylbutyl)-p-phenylenediamine (NOCRAC 6C), manufactured by OUCHI SHINKO CHEMICAL INDUSTRIAL CO., LTD.
*2: 2,2,4-Trimethyl-1,2-dihydroquinoline polymer (NOCRAC 224), manufactured by OUCHI SHINKO CHEMICAL INDUSTRIAL CO., LTD.
*3: N-Cyclohexylbenzothiazole-2-sulfenamide (NOCCELER CZ), manufactured by OUCHI SHINKO CHEMICAL INDUSTRIAL CO., LTD.
*4: N,N-Dicyclohexylbenzothiazole-2-sulfenamide (NOCCELER DZ), manufactured by OUCHI SHINKO CHEMICAL INDUSTRIAL CO., LTD.

TABLE 4

| | | Comp. Ex. 2 | Comp. Ex. 3 | Comp. Ex. 10 | Comp. Ex. 11 | Comp. Ex. 12 | Comp. Ex. 13 |
|---|---|---|---|---|---|---|---|
| Properties of unvulcanized rubber | t5 | 85 | 100 | 100 | 101 | 93 | 93 |
| | tc (90) | 91 | 100 | 94 | 95 | 95 | 95 |
| | MH | 102 | 100 | 102 | 103 | 103 | 102 |
| Initial properties of vulcanized rubber | Tensile strength | 99 | 100 | 100 | 99 | 101 | 101 |
| | Maximum elongation | 95 | 100 | 95 | 97 | 98 | 98 |
| | Tensile stress at 200% | 102 | 100 | 101 | 102 | 103 | 102 |
| | Hardness | 101 | 100 | 101 | 101 | 101 | 101 |

Examples 14 to 17 and Comparative Examples 4 and 5

The procedure of the above test was repeated, except that different accelerators shown in Table 5 were compounded in a molar amount equal to that of DCBS.

The results on (1) properties of unvulcanized rubber and (2) initial properties of vulcanized rubber were expressed in terms of an index by presuming the results of Comparative Example 5 to be 100. The results are shown in Table 6.

TABLE 5

| | Comp. Ex. 4 | Comp. Ex. 5 | Comp. Ex. 14 | Comp. Ex. 15 | Comp. Ex. 16 | Comp. Ex. 17 |
|---|---|---|---|---|---|---|
| Natural rubber | 100.0 | 100.0 | 100.0 | 100.0 | 100.0 | 100.0 |
| Zinc oxide | 5.0 | 5.0 | 5.0 | 5.0 | 5.0 | 5.0 |
| Stearic acid | 3.0 | 3.0 | 3.0 | 3.0 | 3.0 | 3.0 |
| HAF | 50.0 | 50.0 | 50.0 | 50.0 | 50.0 | 50.0 |
| Napthenic oil | 10.0 | 10.0 | 10.0 | 10.0 | 10.0 | 10.0 |
| 6PPD *1 | 2.0 | 2.0 | 2.0 | 2.0 | 2.0 | 2.0 |
| TMDQ *2 | 1.0 | 1.0 | 1.0 | 1.0 | 1.0 | 1.0 |
| Sulfur | 3.0 | 3.0 | 3.0 | 3.0 | 3.0 | 3.0 |
| CBS *3 | 0.76 | — | — | — | — | — |
| DCBS *4 | — | 1.0 | — | — | — | — |
| BMBS | — | — | 0.73 | — | — | — |
| BEBS | — | — | — | 0.77 | — | — |
| BPBS | — | — | — | — | 0.81 | — |
| BBBS | — | — | — | — | — | 0.85 |

TABLE 6

|  |  | Comp. Ex. 4 | Comp. Ex. 5 | Comp. Ex. 14 | Comp. Ex. 15 | Comp. Ex. 16 | Comp. Ex. 17 |
|---|---|---|---|---|---|---|---|
| Properties of unvulcanized rubber | t5 | 91 | 100 | 98 | 100 | 104 | 104 |
|  | tc (90) | 91 | 100 | 98 | 100 | 102 | 105 |
|  | MH | 97 | 100 | 97 | 100 | 99 | 97 |
| Initial properties of vulcanized rubber | Tensile strength | 101 | 100 | 101 | 101 | 100 | 100 |
|  | Maximum elongation | 100 | 100 | 101 | 100 | 100 | 99 |
|  | Tensile stress at 200% | 100 | 100 | 99 | 100 | 99 | 100 |
|  | Hardness | 100 | 100 | 100 | 100 | 100 | 101 |

The results of the preliminary test shown in Table 2 show that BEBS (180 times in 22 days) had much lower bioaccumulation or bioconcentration than DCBS (6000 times). The results of Tables 4 and 6 show that the rubber compositions compounded with N-alkyl-N-t-butylbenzothiazole-2-sulfenamide which is the vulcanization accelerator according to the present invention had a vulcanization retarding effect favorably comparable with DCBS (Comparative Example 2). Further, as can be seen from the results in Table 6, the vulcanization accelerator according to the present invention, particularly BEBS, provides the same properties of unvulcanized rubber and initial properties of vulcanized rubber as DCBS by regulating the amount of the vulcanization accelerator depending upon the molecular weight and compounding the vulcanization accelerator in a molar amount equal to that of DCBS.

The invention claimed is:

1. An N-alkyl-N-t-butylbenzothiazole-2-sulfenamide represented by formula [I]:

[Chemical formula 1]

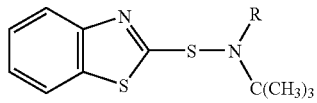

[I]

wherein R represents ethyl, n-propyl, or n-butyl.

2. A vulcanization accelerator for rubber comprising an N-alkyl-N-t-butylbenzothiazole-2-sulfenamide represented by formula [II]:

[Chemical formula 2]

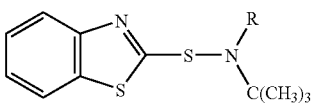

[II]

wherein R represents ethyl, n-propyl, or n-butyl.

* * * * *